United States Patent [19]

Kandachi et al.

[11] Patent Number: 4,521,454
[45] Date of Patent: Jun. 4, 1985

[54] METHOD OF PRODUCING HEAT-REFLECTING GLASS PLATE BY COATING WITH TITANIUM OXIDE FILM

[75] Inventors: Takayoshi Kandachi; Seiki Okino; Toshiharu Yanai; Katsuto Tanaka, all of Matsusaka, Japan

[73] Assignee: Central Glass Company, Limited, Ube, Japan

[21] Appl. No.: 577,379

[22] Filed: Feb. 6, 1984

[30] Foreign Application Priority Data

Feb. 12, 1983 [JP] Japan .................. 58-20563

[51] Int. Cl.$^3$ .................. B05D 5/06; B05D 3/02
[52] U.S. Cl. .................. 427/168; 65/60.5 Z; 427/314; 427/389.7
[58] Field of Search .................. 427/168, 398.1, 314, 427/389.7; 65/60.52

[56] References Cited

U.S. PATENT DOCUMENTS 4,241,108 12/1980 Tracy et al. .................. 427/168 X
4,323,598 4/1982 Okino et al. .................. 427/168 X

FOREIGN PATENT DOCUMENTS 2621587 11/1976 Fed. Rep. of Germany ...... 427/168
54-047715 4/1979 Japan .................. 427/168
1510587 5/1978 United Kingdom .
2018234 10/1979 United Kingdom .

*Primary Examiner*—Thurman K. Page
*Attorney, Agent, or Firm*—Schwartz, Jeffery, Schwaab, Mack, Blumenthal & Evans

[57] ABSTRACT

To produce a heat-reflecting glass plate by coating a glass plate surface with a titanium oxide film, a solution of a thermally decomposable organic titanium compound is sprayed onto the glass plate surface while the glass plate is kept heated. As the improvement, use is made of a chelate compound of titanium formed by coordination of two molecules of either acetylacetone or ethyl acetoacetate as chelate ligands and two molecules of a polyalcohol as nonchelate ligands to a titanium atom. Preferably the polyalcohol is a 1,3-diol, and particularly 2-ethyl-1,3-hexane diol. This chelate compound is not easily influenced by moisture and gives a titanium oxide coating film of superior quality.

4 Claims, No Drawings

METHOD OF PRODUCING HEAT-REFLECTING GLASS PLATE BY COATING WITH TITANIUM OXIDE FILM

BACKGROUND OF THE INVENTION

This invention relates to the production of a heat-reflecting glass plate, and more particularly to a method of coating a glass plate surface with a titanium oxide film by spraying a solution of a thermally decomposable organic compound of titanium onto a heated glass surface.

Titanium oxide is a typical coating material for producing a heat-reflecting glass plate. A well known method for coating one side of a glass plate with a titanium oxide film is the spraying of a solution of a thermally decomposable organic compound of titanium onto the glass surface while the glass plate is sufficiently heated. The titanium compound in the sprayed solution undergoes thermal decomposition on the heated glass surface to form titanium oxide. An example of the titanium compounds conventionally used for this purpose is alkoxyacetylacetonato titanium which is obtained by reaction of titanium with a monoalcohol and acetylacetone.

In industrial practice, however, the titanium oxide coating film formed by the above described method is often unsatisfactory in the closeness or strength of adhesion to the glass surface and/or smoothness of the coating film surface. An important cause of such defects in the titanium oxide coating film is considered to be partial hydrolysis pf the titanium compound in the spraying solution because of susceptibility of the titanium compound to moisture present in the spraying atmosphere and even in the solution. Therefore, strict control of humidity becomes a requisite for the spray coating operation and also for the preparation and maintenance of the titanium compound solution. However, the exercise of such humidity control becomes a cause of lowering of the productivity, and this is a matter of serious concern particularly in the case of continuously producing heat-reflecting glass sheet by performing the spray coating operation before cooling of a glass sheet travelling along a continuous glass sheet production line.

SUMMARY OF THE INVENTION

It is an object of the present invention to make an improvement in the above described method of coating a glass plate with a heat-reflecting titanium oxide film with a view to avoiding adverse influences of moisture without sacrificing the productivity.

A method according to the invention is for coating a glass plate surface with a titanium oxide film to produce a heat-reflecting glass plate and comprises the step of spraying a solution of a thermally decomposable organic compound of titanium in an organic solvent onto a surface of the glass plate which is at such an elevated temperature that the titanium compound in the sprayed solution decomposes on the glass plate surface to form titanium oxide. The method of the invention is characterized in that the titanium compound is a chelate compound of titanium formed by coordination of two chelate ligands, which are selected from acetylacetone and ethyl acetoacetate, and two nonchelate ligands, which are a polyhydric alcohol, to a titanium atom.

It is desirable that the polyhydric alcohol as the nonchelate ligands is a 1,3-diol, and 2-ethyl-1,3-hexane diol is preferred to other 1,3-diols.

The titanium compound employed in the present invention is practically insusceptible to moisture and, when applied to a heated glass surface by a known spraying method, readily undergoes thermal decomposition to give a titanium oxide coating film of good quality. By using this invention it becomes easy to coat a glass plate surface with a titanium oxide film excellent in appearance, surface smoothness and the manner of adhesion to the glass surface. From an industrial point of view, an important merit of this invention is that the burden of the humidity control on the spray coating process can greatly be lessened and consequently the productivity can be improved.

We have carried out extensive studies on various kinds of organic titanium compounds with respect to the degree of susceptibility to moisture. As mentioned hereinbefore, if the titanium compound used in the spray coating method to which the invention relates undergoes partial hydrolysis before thermally decomposing on the glass surface the resultant coating film is often unsatisfactory in the manner of adhesion to the glass surface and/or the smoothness of the coating film surface. Besides, the hydrolyzed portion of the titanium compound tends to polymerize to form a macromolecular substance which intrudes in the titanium oxide coating film to produce a number of opaque spots.

First we have confirmed that a group of organic titanium compounds in which either acetylacetone or ethyl acetoacetate coordinates to titanium are relatively high in stability of coordination bonds and less susceptible to moisture than titanium compounds formed by coordination of other kinds of $\beta$-diketo or $\beta$-ketoester compounds such as benzoylacetone, dibenzoylacetone and dipivaloylacetone, and that particularly when either acetylacetone or ethyl acetoacetate molecules are coordinating as chelate ligands to a titanium atom these titanium compounds are superior in stability in the presence of moisture.

A chelate compound of tianium suitable for use in forming titanium oxide by pyrolysis is obtained by coordination of two molecules of an alcohol as nonchelate ligands in combination with two molecules of either acetylacetone or ethyl acetoacetate as chelate ligands. We have discovered that such a chelate compound becomes less susceptable to moisture when the coordinated alcohol is a polyalcohol than in the case of a monoalcohol, and that the coordination of a 1,3-diol such as 1,3-butane diol, 2,2-dimethyl-1,3-propane diol or 2-ethyl-1,3-hexane diol gives a titanium compound almost insusceptible to moisture, though the use of a different diol such as 1,2-butane diol or 1,4-butane diol is also advantageous over the use of a monoalcohol. Presumably the superiority of 1,3-diols among polyalcohols is attributed to the length of the distance between the two OH-groups. Among 1,3-diols, 2-ethyl-1,3-hexane diol is the most favorable in view of its large molecular weight and strong force of coordination bond and also best results obtained in many experiments. In the chelate compounds of titanium used in this invention, the diol is required to be coordinating as nonchelate ligands. We have confirmed that similar chelate compounds of titanium formed by coordination of a diol as chelate ligands are not always very stable in the presence of moisture.

A chelate compound of titanium having the above specified chelate and nonchelate ligands is hardly influenced by moisture. Therefore, the coating process according to the invention can be accomplished without suffering from hydrolysis and succeeding polymerization of the titanium compound in the spraying solution even though some moisture is present in the spraying atmosphere and possibly in the solution too, whereby a heat-reflecting glass plate of good quality can easily be produced.

DESCRIPTION OF THE PREFERRED EMBODIMENTS

In the coating method according to the invention use is made of a chelate compound of a specific type as described above, but this method does not substantially differ in operation procedures from the conventional titanium oxide coating methods using solutions of different compounds of titanium.

First a solution for spraying is prepared by dissolving a selected chelate compound of titanium, such as 2-ethyl-1,3-hexane-dioxy diacetylacetonato titanium for example, in a suitable organic solvent such as dichloromethane for example. It is also possible to form a desired chelate compound of titanium at the stage of preparing a spraying solution by using an intermediate titanium compound having acetylacetone or ethyl acetoacetate molecules as chelate ligands and monoalkoxyl groups as nonchelate ligands and by substituting a suitable polyalcohol for the monoalkoxyl groups, as can be seen in Examples presented hereinafter. In any case, the titanium compound subjected to spraying and thermal decomposition in the coating method of the invention has no monoalcohol molecule or monoalkoxyl group.

Using a conventional spraying apparatus, the solution is sprayed onto a major surface of a heated glass plate. Heating of the glass plate may be continued during the spray coating operation, but this is not a requisite. That is, the glass plate may be only preheated and subjected to spray coating while undergoing natural cooling. In either case the surface temperature of the glass plate should be high enough to bring about thermal decomposition of the titanium compound in the sprayed solution to form titanium oxide. A suitable range of the glass surface temperature is from about 500° C. to about 600° C.

The invention will further be illustrated by the following nonlimiting examples.

EXAMPLE 1

As the starting material for an intended chelate compound of titanium, use was made of a mixture of dipropoxydiacetylacetonato titanium and free propyl alcohol in the proportion indicated by $[Ti(O_2C_5H_7)_2(OC_3H_7)_2+2C_3H_7OH]$. Acetylacetone and 2-ethyl-1,3-hexane diol were successively added to the starting material, and then dichloromethane selected as solvent was added. The resultant mixture was composed of 19.5% of the starting material $[Ti(O_2C_5H_7)_2(OC_3H_7)_2+2C_3H_7OH]$, 5.7% of acetylacetone, 17.0% of 2-ethyl-1,3-hexane diol and 57.8% of dichloromethane, by volume. This mixture was stirred to obtain a solution for use in spray coating.

The addition of acetylacetone to the starting material was based on the chemical equilibrium theory and for the purpose of preventing the acetylacetone molecules in chelate coordination with titanium in the starting material from being substituted by either coexisting free propyl alcohol or the subsequently added diol. As mentioned hereinbefore, a chelate compound of titanium having either acetylacetone or ethyl acetoacetate as chelate ligands and a polyalcohol as nonchelate ligands is excellent in stability in the presence of moisture. When making the coordination of the diol to titanium subsequently to the coordination of acetylacetone (or ethyl acetoacetate) as in this example, the presence of excess acetylacetone or ethyl acetoacetate in the liquid reaction system is necessary to keep the chelate ligands in the coordinated state. As to the proportion of the added acetylacetone (or ethyl acetoacetate when it is employed as chelate ligands in the starting material) to the starting material $[Ti(O_2C_5H_7)_2(OC_3H_7)_2+2C_3H_7OH]$, a suitable range is from 0.1 to 0.35 by volume. When the proportion of free acetylacetone is less than 0.1 it is difficult to surely prevent the aforementioned substitution, but an increase of the proportion of free acetylacetone beyond 0.35 produces no additional effect. We have confirmed by experiments that the added free acetylacetone or ethyl acetoacetate does not substitute for the monoalcohol ccordinating as nonchelate ligands, irrespective of the amount of the added compound.

In this example the addition of 2-ethyl-1,3-hexane diol, a preferred polyalcohol, to the mixture of the starting material and acetylacetone results in that the diol substitutes for the propoxyl groups initially coordinated to titanium in the starting material. Accordingly the chelate compound of titanium in the starting material converts into another chelate compound in which two molecules of acetylacetone are coordinating as chelate ligands to titanium and two moleculates of the diol as nonchelate ligands. A solution of this chelate compound of titanium is obtained by the addition of dichloromethane, a preferred solvent. A suitable amount of the polyalcohol used in this method is variable depending on the kind of the polyalcohol. In the case of 2-ethyl-1,3-hexane diol it is suitable that the proportion of the diol to the starting material is in the range from 0.5 to 1.3 by volume.

Using a conventional spraying apparatus and humidity controlled compressed air, the solution prepared in this example was sprayed onto a major surface of a soda-lime glass plate produced by the float process. In the spraying operation the glass plate was kept at about 570° C., and the moisture content in the spraying atmosphere was controlled to 10 g/m$^3$ (at N.T.P.) in the first run but increased to 25 g/m$^3$ (at N.T.P.) in the second run.

In either of the thus produced two samples of heat-reflecting glass plate, the titanium oxide coating film was exellent in both the manner of adhesion to the glass plate and the smoothness of the surface.

EXAMPLE 2

A solution was prepared by using the same materials as in Example 1 in different proportions. That is, the solution was obtained from a mixture composed of 20.8% of the starting material $[Ti(O_2C_5H_7)_2(OC_3H_7)_2+2C_3H_7OH]$, 2.5% of acetylacetone, 23.2% of 2-ethyl-1,3-hexane diol and 53.5% of dichloromethane, by volume. This solution was used in the same spray coating operation as in Example 1.

In the two samples produced by controlling the moisture content in the spraying atmosphere to 10 g/m$^3$ and 25 g/m$^3$, respectively, the titanium oxide coating film was excellent in both the manner of adhesion to the glass plate and the smoothness of the surface.

EXAMPLE 3

The starting material was a mixture of titanium dipropoxy-di(ethyl acetoacetate) and free propyl alcohol in the proportion indicated by $[Ti(O_3C_6H_9)_2(OC_3H_7)_2 + 2C_3H_7OH]$. Ethyl acetoacetate and 2-ethyl-1,3-hexane diol were successively added to the starting material, and then dichloromethane was added. The resultant mixture was composed of 20.1% of the starting material, 6.6% of ethyl acetoacetate, 11.7% of 2-ethyl-1,3-hexane diol and 61.6% of dichloromethane, by volume. Obtained as the result was a solution of a chelate compound in which two molecules of ethyl acetoacetate are coordinating as chelate ligands to titanium and two molecules of the diol as nonchelate ligands.

This solution was used in the same spray coating operation as in Example 1. In either of the two samples produced by differently controlling the moisture content in the spraying atmosphere, the titanium oxide coating film was excellent in both the manner of adhesion to the glass plate and the smoothness of the surface.

REFERENCE 1

A solution was prepared generally in accordance with Example 1 except that the addition of free acetylacetone was omitted. That is, the solution was obtained from a mixture composed of 21% of the starting material $[Ti(O_2C_5H_7)_2(OC_3H_7)_2 + 2C_3H_7OH]$, 18% of 2-ethyl-1,3-hexane diol and 61% of dichloromethane, by volume. This solution was used in the same spray coating operation as in Example 1.

In the sample produced by controlling the moisture content in the spraying atmosphere to 10 g/m$^3$ the titanium oxide coating film was excellent in both the manner of adhesion to the glass plate and the smoothness of the surface. However, when the moisture content was 25 g/m3 the resultant coating film was unacceptably inferior in the adhesion and barely acceptable in the smoothness of the surface.

REFERENCE 2

A solution was prepared generally in accordance with Example 1 except that the addition of 2-ethyl-1,3-hexane diol was omitted. That is, the solution was obtained from a mixture composed of 23% of the starting material described in Example 1, 7% of free acetylacetone and 70% of dichloromethane, by volume. In this case no substitution took place for the two propoxyl groups (monoalcohol) initially coordinated to titanium as nonchelate ligands.

This solution was used in the same spray coating operation as in Example 1. In the sample produced by controlling the moisture content to 10 g/m$^3$ the titanium oxide coating film was unsatisfactory in the manner of adhesion though acceptable in the smoothness of the surface. When the moisture content was 25 g/m$^3$ the coating film was unsatisfactory in both the adhesion and the surface smoothness.

REFERENCE 3

Instead of acetylacetone a different $\beta$-diketone, benzoyl acetone, was used as the chelate ligands to coordinate to titanium in preparing the starting material. That is, the starting material in this experiment was a mixture indicated by $[Ti(O_2C_{10}H_{10})_2(OC_3H_7)_2 + 2C_3H_7OH]$. Benzoyl acetone and 2-ethyl-1,3-hexane diol were successively added to the starting material, and then dichloromethane was added. The resultant mixture was composed of 25% of the starting material, 7.5% of benzoyl acetone, 14.5% of 2-ethyl-1,3-hexane diol and 53% of dichloromethane, by volume. A solution prepared from these materials was used in the same spray coating operation as in Example 1.

In the sample produced by controlling the moisture content in the spraying atmosphere to 10 g/m$^3$ the titanium oxide coating film was excellent in both the manner of adhesion and the smoothness of the surface. However, when the moisture content was 25 g/m$^3$ the coating film was unsatisfactory in the adhesion though acceptable in the smoothness of the surface.

REFERENCE 4

In this case the starting material was 2-ethyl-1,3-hexane-dioxytitanium. A solution was prepared from a mixture of 25% of 2-ethyl-1,3-hexane-dioxytitanium, 12% of propyl alcohol and 63% of dichloromethane, by volume. Therefore, neither acetylacetone nor ethyl acetoacetate coordinated to titanium. The solution was used in the same spray coating operation as in Example 1.

In the sample produced by controlling the moisture content in the spraying atmosphere to 10 g/m$^3$ the titanium oxide coating film was excellent in the manner of adhesion but unsatisfactory in the smoothness of the surface. When the moisture content was 25 g/m$^3$ the coating film was unsatisfactory both in the adhesion and the surface smoothness.

What is claimed is:

1. A method of coating a glass plate surface with a titanium oxide film to produce a heat-reflecting glass plate, the method having the step of spraying a solution of a thermally decomposable organic compound of titanium in an organic solvent onto a surface of a glass plate which is at such an elevated temperature that said compound in the sprayed solution decomposes on the glass plate surface to form titanium oxide, characterized in that said compound is a chelate compound of titanium formed by coordination of two chelate ligands, which are selected from the group consisting of acetylacetone and ethyl acetoacetate, and two nonchelate ligands, which are a polyhydric alcohol, to a titanium atom.

2. A method according to claim 1, wherein said polyhydric alcohol is a 1,3-diol.

3. A method according to claim 2, wherein said 1,3-diol is 2-ethyl-1,3-hexane diol.

4. A method according to claim 1, wherein said solvent comprises dichloromethane.

* * * * *